United States Patent
Smeed

(10) Patent No.: US 10,729,602 B2
(45) Date of Patent: Aug. 4, 2020

(54) MODULAR CRITICAL CARE ADAPTOR FOR LITTERS

(71) Applicant: Smeed Technologies LLC, Cumming, GA (US)

(72) Inventor: Eric M. Smeed, Cumming, GA (US)

(73) Assignee: SMEED TECHNOLOGIES LLC, Cumming, GA (US)

( * ) Notice: Subject to any disclaimer, the term of this patent is extended or adjusted under 35 U.S.C. 154(b) by 952 days.

(21) Appl. No.: 15/147,857

(22) Filed: May 5, 2016

(65) Prior Publication Data

US 2016/0324702 A1 Nov. 10, 2016

Related U.S. Application Data

(60) Provisional application No. 62/157,955, filed on May 6, 2015, provisional application No. 62/159,419, filed on May 11, 2015, provisional application No. 62/202,963, filed on Aug. 10, 2015.

(51) Int. Cl.
| | |
|---|---|
| *A61G 1/04* | (2006.01) |
| *F16M 13/02* | (2006.01) |
| *F16M 11/24* | (2006.01) |
| *A61M 5/14* | (2006.01) |
| *F16B 2/06* | (2006.01) |

(52) U.S. Cl.
CPC ............... *A61G 1/04* (2013.01); *F16M 11/24* (2013.01); *F16M 13/02* (2013.01); *F16M 13/022* (2013.01); *A61G 2203/78* (2013.01); *A61M 5/1417* (2013.01); *F16B 2/065* (2013.01)

(58) Field of Classification Search
CPC .. A61G 1/04; A61G 2203/78; A61G 2210/30; A61G 7/05; F16M 13/02
See application file for complete search history.

(56) References Cited

U.S. PATENT DOCUMENTS

| | | | | |
|---|---|---|---|---|
| 3,427,668 A | * | 2/1969 | Mcmanus, Jr. | ........ A61G 12/00 5/182 |
| 4,113,218 A | * | 9/1978 | Linder | .................... A61G 13/10 248/124.1 |
| 4,557,453 A | | 12/1985 | McCloskey | |
| 4,747,172 A | * | 5/1988 | Hohol | ...................... A61G 7/05 206/557 |
| 5,152,486 A | * | 10/1992 | Kabanek | ................ A61G 13/10 108/49 |

(Continued)

OTHER PUBLICATIONS

Nickitas-Etienne, "International Preliminary Report on Patentability issued in International Application No. PCT/UD2016/031073", dated Nov. 7, 2017, 8 pages.

(Continued)

*Primary Examiner* — Eric J Kurilla
(74) *Attorney, Agent, or Firm* — Johnson, Marcou, Isaacs & Nix, LLC

(57) ABSTRACT

A modular approach to mounting medical equipment on evacuation litters employs litter engagement members of various configuration and a plurality of rail members all having the same sectional profile. The rail members can be mounted to a variety of connectors and auxiliary pieces such that equipment supporting structures can be built on a patient bearing litter without sacrificing access to the patient.

22 Claims, 16 Drawing Sheets

(56) References Cited

U.S. PATENT DOCUMENTS

| | | | |
|---|---|---|---|
| 5,845,351 A * | 12/1998 | Berta | A61G 1/04 5/626 |
| 6,431,505 B2 | 8/2002 | Chinn | |
| 6,446,285 B1 * | 9/2002 | Chinn | A61G 1/04 108/49 |
| 6,493,890 B2 * | 12/2002 | Smeed | A61G 1/04 108/49 |
| 6,708,935 B2 | 3/2004 | Smeed | |
| 6,842,922 B2 | 1/2005 | Smeed | |
| 7,458,743 B2 | 12/2008 | Smeed | |
| 8,950,344 B2 * | 2/2015 | Lewis | A61G 13/101 108/179 |
| 2003/0115671 A1 * | 6/2003 | Smeed | A61G 1/04 5/503.1 |
| 2003/0143052 A1 * | 7/2003 | Fehrle | A61G 1/06 410/46 |
| 2009/0260159 A1 * | 10/2009 | Buchanan | A61G 1/013 5/617 |
| 2010/0139005 A1 * | 6/2010 | Perez | A61G 1/04 5/658 |
| 2010/0146702 A1 | 6/2010 | Sherman | |
| 2012/0241571 A1 * | 9/2012 | Masionis | A61G 1/04 248/214 |
| 2012/0304390 A1 * | 12/2012 | Perez | A61G 1/04 5/658 |
| 2017/0246059 A1 * | 8/2017 | Chinn | A47C 19/02 |
| 2018/0000666 A1 * | 1/2018 | Sirkin | A61G 1/04 |
| 2018/0104120 A1 * | 4/2018 | Sirkin | A61G 1/04 |
| 2018/0110662 A1 * | 4/2018 | Doak | A61G 1/04 |
| 2018/0360675 A1 * | 12/2018 | Darrah | A61G 1/06 |

OTHER PUBLICATIONS

Young, "International Search Report and Written Opinion issued in International Application No. PCT/US2016/031073", dated Aug. 12, 2016, 9 pages.

* cited by examiner

MODULAR CRITICAL CARE ADAPTOR FOR LITTERS

This application claims priority from U.S. Provisional Patent Application No. 62/157,955, filed May 6, 2015; also U.S. Provisional Patent Application No. 62/159,419, filed May 11, 2015; and, U.S. Provisional Patent Application No. 62/202,963, filed Aug. 10, 2015, all of which are incorporated herein by reference.

FIELD OF INVENTION

This invention relates to a structure for attaching to litters, including litters that meet NATO standards as well as civilian emergency medical litters, and for holding medical equipment useful in the care and/or transport of patients between locations. Further various components may be useful in mounting to alternative surfaces such as walls and vehicles or in temporary intensive care units in combat support hospitals.

BACKGROUND

The standard litter in use is the NATO litter or a modified version of the NATO litter. A common feature between the NATO litter and most modified versions is a two pole structure running in parallel to each other the length of an area to carry and support a patient such as nylon as illustrated in FIGS. 1 and 2 showing the prior art. Usually, these litters are used in evacuating injured and/or wounded patients from their location of injury (or far forward facility) to a care facility for treatment. During transport, it is vital to monitor a patient's current medical status to allow medical personnel to attempt to maintain the status quo, which preferable is sufficiently stable to allow for transport. Civilian emergency responders may use litters developed by Stryker Corporation. In either case, a need continues to exist for an efficient and effective way to attach medical equipment to a transportable litter.

Prior to my earlier development of critical care platforms for litters, litters did not allow for the attachment of medical monitoring equipment given their structure of two poles and a place for the patient, which usually is canvas or a similar material. Instead of two individuals moving a patient, it would take at least one additional person to move alongside the litter to move the equipment connected to the patient. Or the extra person may not be needed, because the equipment is put on top of the patient, which is not advisable in most medical situations given the weight of the equipment and notwithstanding the weight, the equipment may shift around on the patient and/or fall off of the patient and the litter. None of these possibilities associated with using the patient as the carrying platform are beneficial to treating the patient.

The present invention is an improvement over my past inventions as shown in U.S. Pat. No. 7,458,743 "Critical care platform for litters"; U.S. Pat. No. 6,842,922 "Critical care platform for litters"; and U.S. Pat. No. 6,493,890 "Critical care platform for litters" all of which addressed the above problems and incorporated herein by reference. One substantial drawback to my prior devices, as may be seen in FIGS. 1 and 2, has been that they sacrificed a certain amount of access to the patient once the devices were placed on the litter.

Notwithstanding the usefulness of the above-described approaches, a need still exists for improvements in lightweight attachment for litters that will allow particular equipment to be transported with the patient without requiring another individual to carry the equipment beyond the two individuals carrying the litter.

SUMMARY OF THE INVENTION

The present invention provides a light weight modular system that can be deployed in a variety of configurations with minimal loss of access to the patient on the litter by virtue of the unique interchangeable modular system. The system uses standardized rails and receivers that are readily secured to each other by locking mechanisms that are retained in place and are not susceptible to being lost or ill-fitting. The rail and receiver structural foundation extends into a plurality of connecting units that allow selective orientation of structural members based on the care giver's need in mounting equipment for a specific patient, thus treatment is not dictated by the equipment mounting regime but rather the equipment mounting regime can be modified by the needs of the patient.

BRIEF DESCRIPTION OF THE DRAWINGS

Referring to the drawings which are appended hereto and which form a portion of this disclosure, it may be seen that.

DETAILED DESCRIPTION

One or more of the objects of the invention can be achieved, at least in part, by providing a platform which preferably attaches to the litter or other patient carrying mechanism, while also preferably being able to stand on its own when not attached to a litter or other patient carrying mechanism. The platform and its different embodiments are a means for supporting and positioning medical equipment to the side and/or above the patient on the patient carrying device. Preferably, the at least one litter adapter allows for at least one piece of medical equipment, device(s), and/or container(s) such as monitors, pumps, ventilators, suction units, IV bags, oxygen bottles to be attached to the litter separately from the platform.

Figure 1:
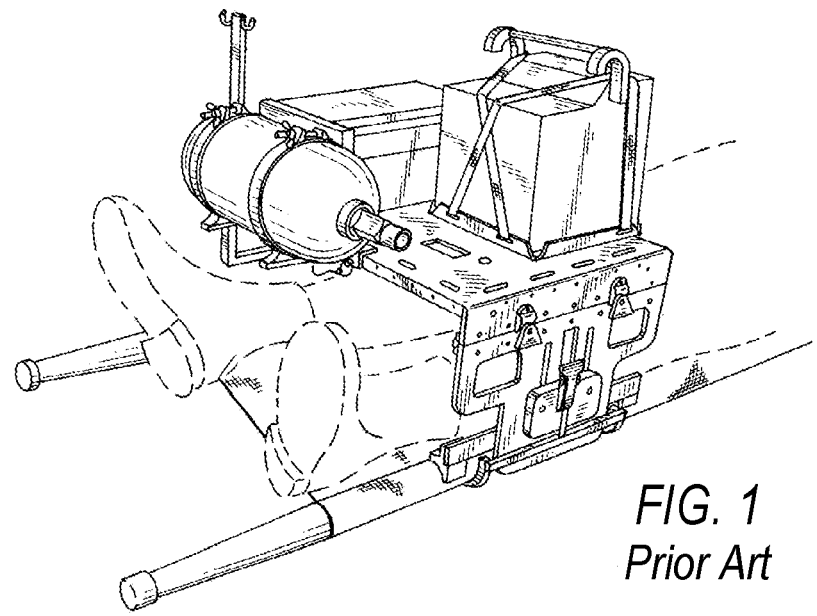
FIGS. 1 and 2 depict the prior art from my earlier inventions.
Figure 2:
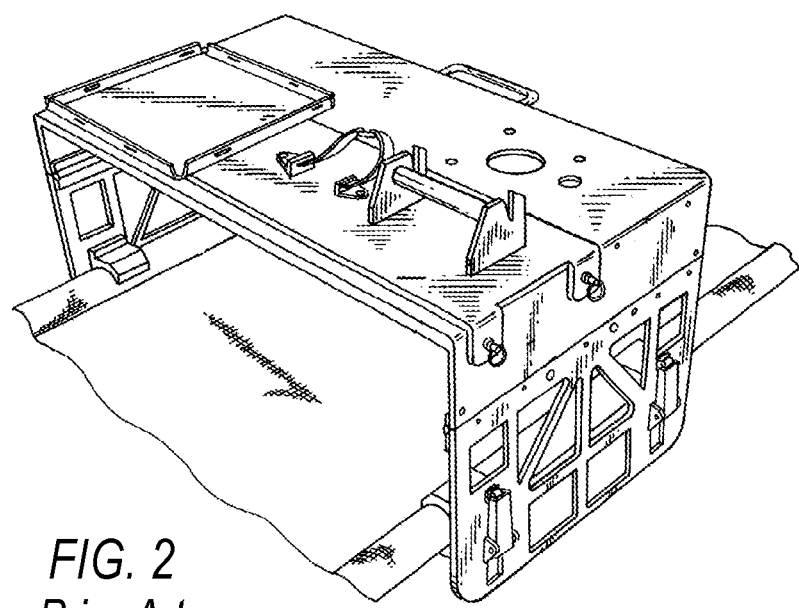
Figure 3A:
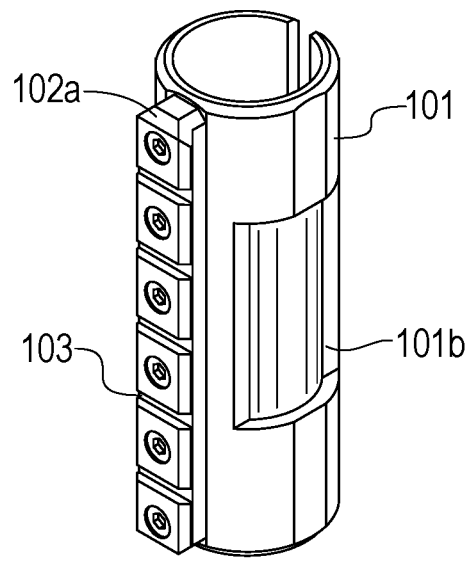
FIGS. 3A to 3D are perspective views depicting one embodiment of NATO litter adapters.
Figure 3B:
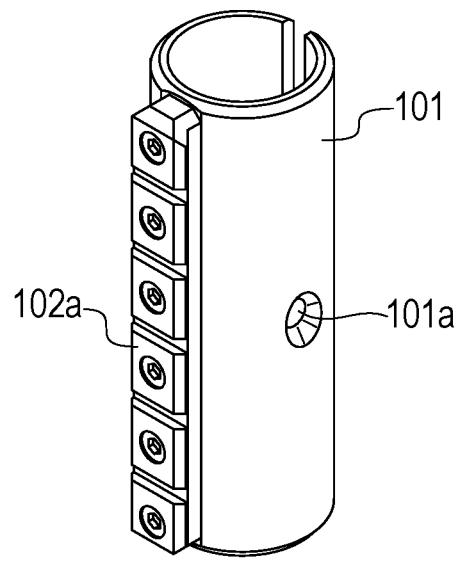
Figure 3C:
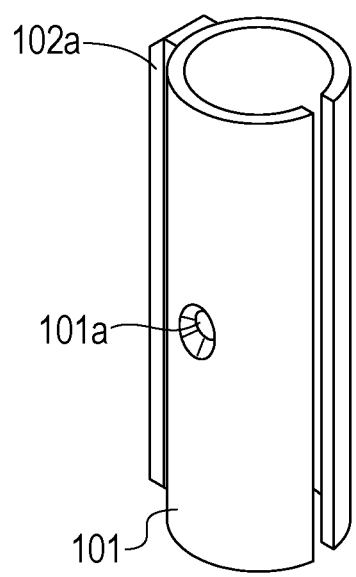
Figure 3D:
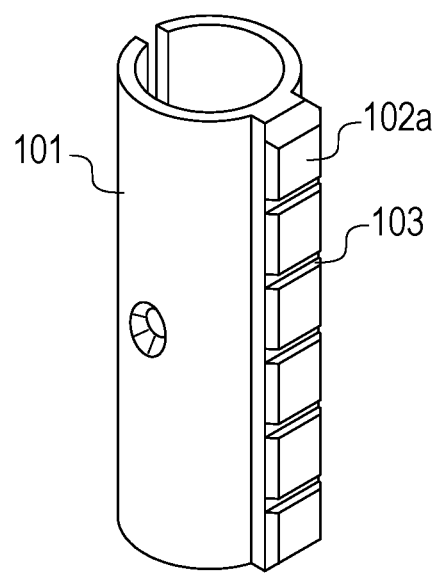
Figure 4:
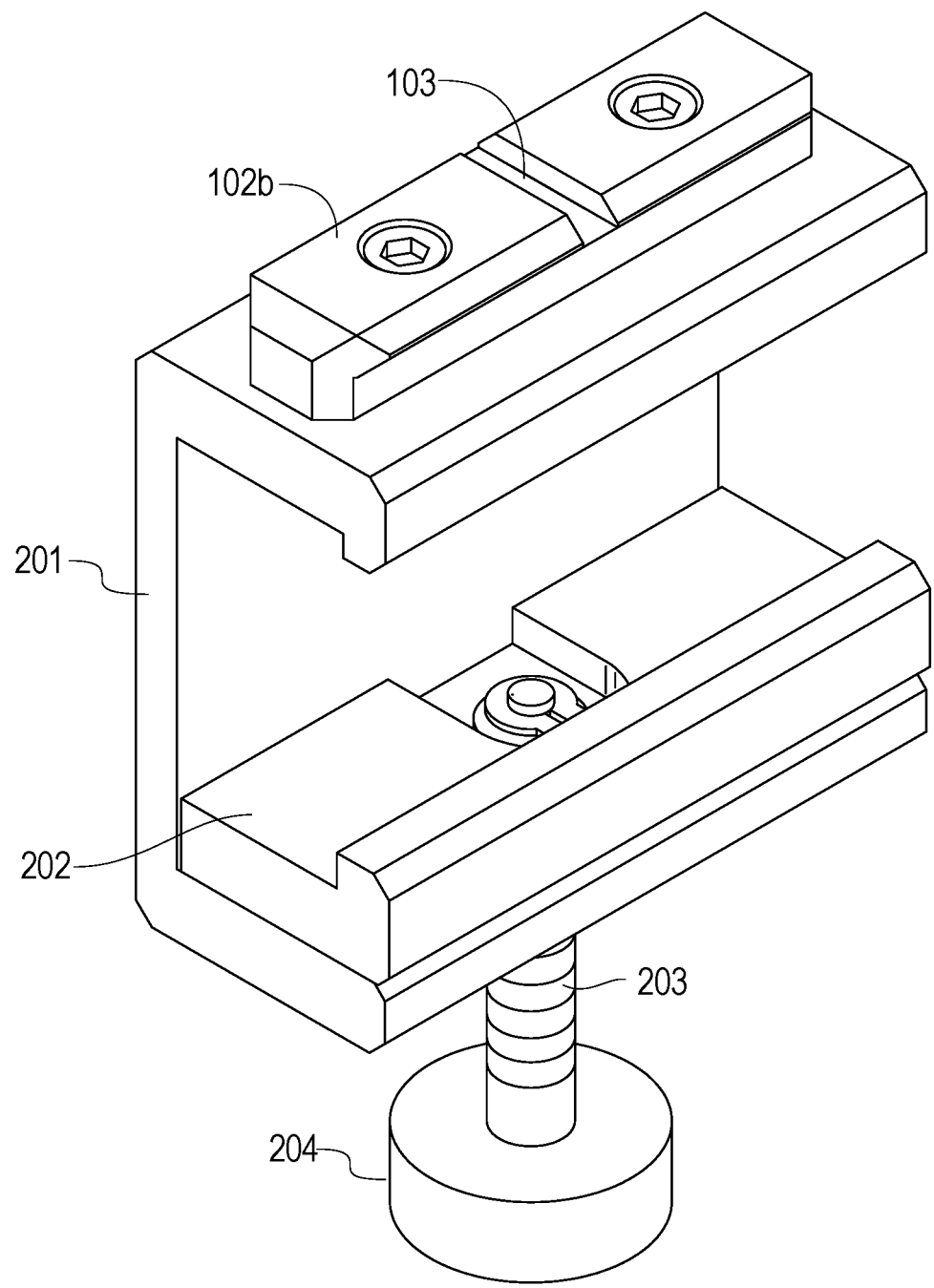
FIG. 4 depicts a Stryker litter adapter.
Figure 7:
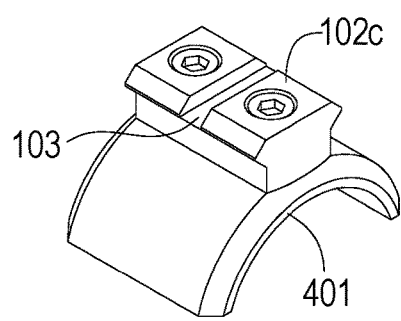
FIG. 7 depicts a second embodiment of a NATO litter interface.

In order to function properly, the modular frame must interface with the litter. Therefore I provide litter interface members to engage the poles of the litters and upon which the equipment mounting structure is built. Referring to FIGS. 3a to 3d, one embodiment of the litter interface members is shown as sleeves 101 which fit onto the poles of the well know NATO litters. As is well known, NATO litters are provided with a fabric or web sling mounted between two poles. The poles are provided with feet proximate each end which are connected by a bolt which runs through the pole and a reinforcing plate and an aperture in the feet to engage a threaded nut. The sleeves 101 are utilized by removing the feet from the NATO litter, sliding the sleeves 101 over the portion of the litter pole adjacent the mounting position of the feet and then replacing the feet and reinforcing plate. The feet, plate and sleeve 101 are then secured to the pole by the original bolt which passes through aperture 101a and cutout 101b which accommodates the NATO plate. A critical component of the modular frame is the use of connecting rails 102. Rails 102 are elongated shaped rails with at least one transverse slot 103 formed in each rail. Referring to FIGS. 3A to 3D, it will be noted that each sleeve 101 has a rail 102a affixed to it. All of the rails in the assembly have the same profile and dimension, however, some rails 102 are longer than others and some may also have a receiver channel 104 formed opposite the slots 103 (see e.g., FIG. 9), for purposes understood more fully from the remainder of the disclosure. FIG. 4 depicts the interface member for a Stryker type litter which does not utilize round poles but rather uses generally rectangular poles. The interface member utilizes a channel member 201 and a movable clamp piece 202 to attach to the Stryker poles. Clamp piece 202 is urged against a pole within channel member 201 by rod 203 which is threadedly engaged with channel member 201 and manually adjusted using knob 204. It will be noted that a standard mounting rail 102b with slot 103 formed therein is affixed to channel member 201. In FIG. 7 another embodiment of a NATO interface member is depicted as a semicircular foot 401 to which a rail 102c is affixed.

Slots 103 formed in the rails 102 inter face with locking mechanisms to secure another component in place on the rail 102. One embodiment of the locking mechanism can be seen in FIGS. 11 and 11A. Lock bar 153 is placed within slot 250 formed in a component, such as a cradle base 191, having a receiver channel 104 formed therein. The slot 250 intersects the receiver channel 104 and a spring well 251 formed in the component. A spring 108 is placed in the well and compressed while lock bar 153 is inserted into slot 250 such that the spring 8 is captured in well 251 and spring detent 153c on the lock bar 153. Lock bar is urged toward the receiver channel 104 such that a locking tab 153b extends into the receiver channel 104. Pivot end 153d is captured within the component while actuator end 153a is exposed so that the locking tab 153b can be moved out of receiver channel 104 by compressing spring 108.

Figure 5:
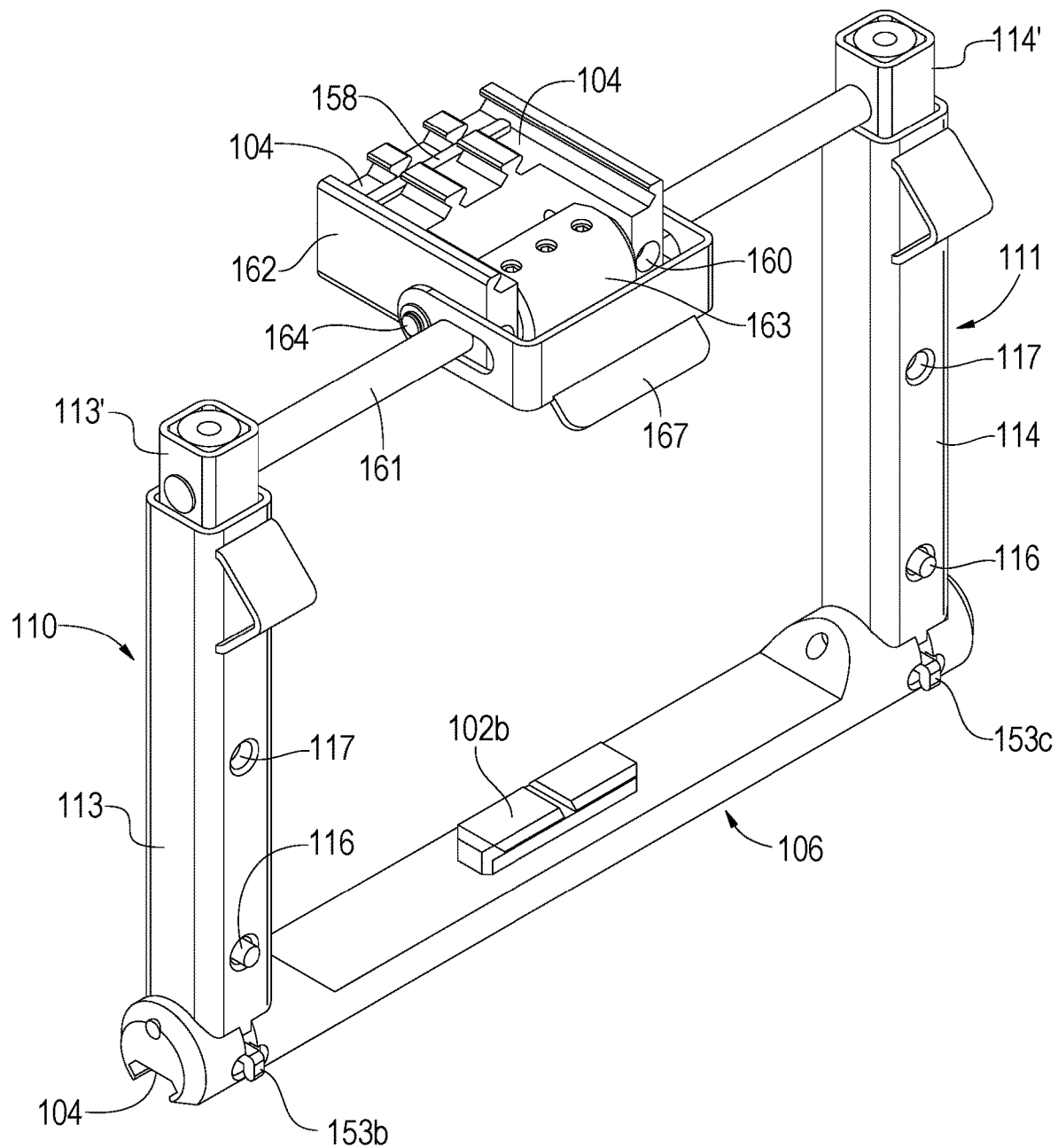
FIG. 5 depicts my rapid jump frame assembly.
Figure 6:
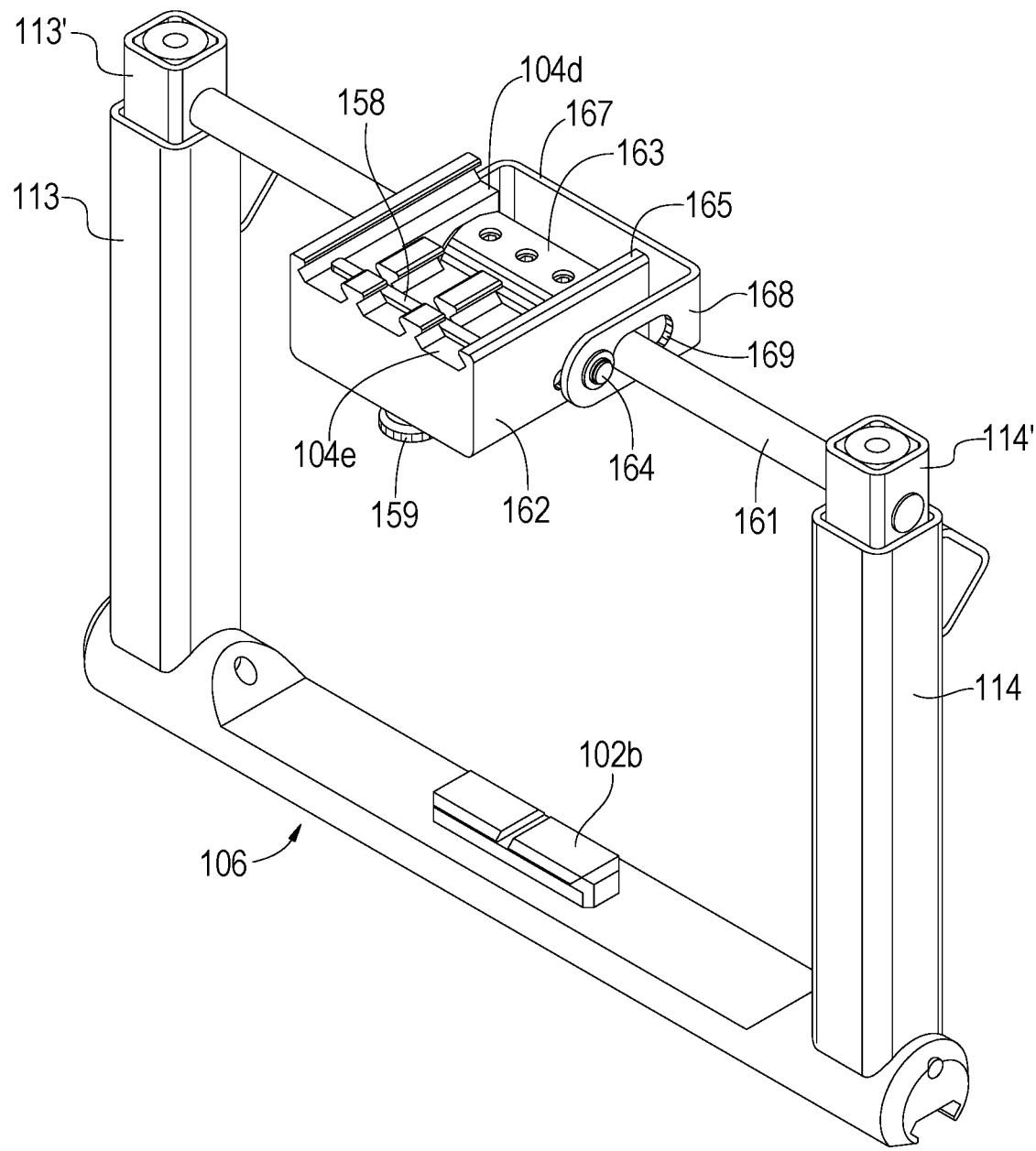
FIG. 6 depicts my rapid jump frame assembly from another side.

Referring to FIGS. 5 and 6 one embodiment of a rapid jump unit assembly is shown. The rapid jump unit assembly allows rapid connection of a frame providing elevation to the litter by engaging the litter interface. It will be noted that the assembly includes a horizontal frame member 106 which defines a receiver channel 104 for receiving one or more rails 102 therein. For example, two of the above described NATO interface members depicted as a semicircular foot 401 (FIG. 7) may be engaged by horizontal frame member with their associated rail 102 locked in place by locking mechanisms using lock bars 153 to releasably engage slots in the interface members. Horizontal frame member 106 supports and is affixed to vertical frame members, 110 and 111, formed by legs 113, 113' and 114, 114' which are telescopic and allow for variation in height above an associated litter. Legs 113' and 114' carry spring loaded detent pins 116 that are selectively engaged in apertures 117 in legs 113 and 114. It will be immediately noted that the present design presents a great improvement in patient access when compared to the earlier designs which substantially blocked lateral access and visibility to the patient beneath the platform. Likewise, the present design provides easy and simple assembly, disassembly and addition to the system.

Figure 8:
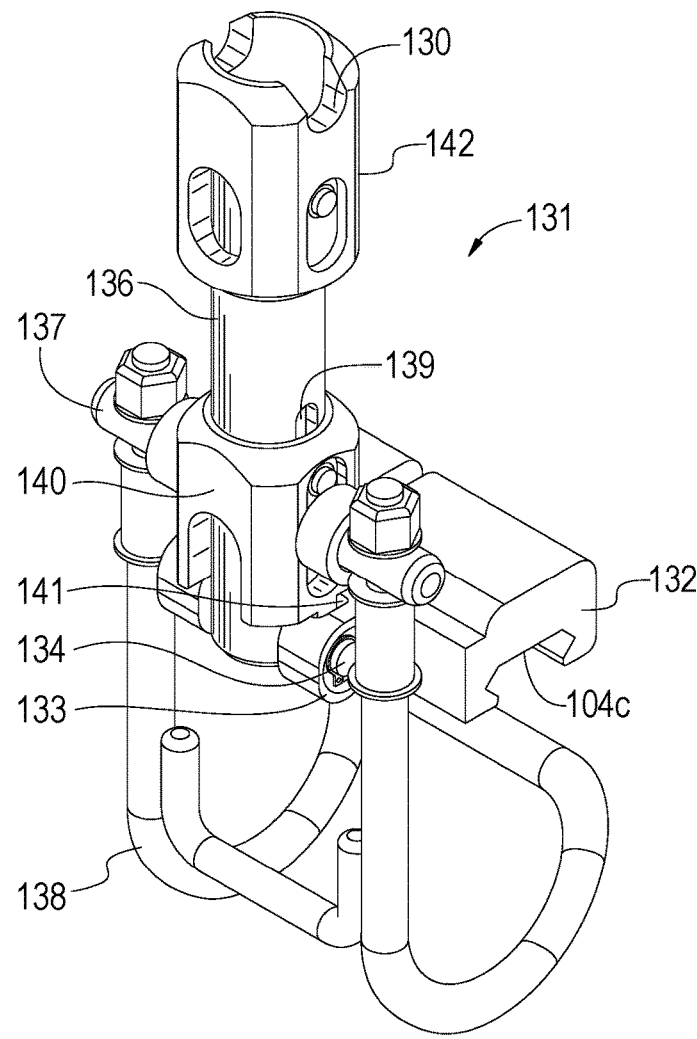
FIG. 8 is a perspective view of my rapid jump frame clamp.

It should be understood that basic building blocks of the system are the mounting rails 102 and mating receivers 104 used to connect the components. These building blocks are used to secure the rapid jump unit assembly to the litter. Horizontal frame member 106 has a mounting rail 102b affixed centrally to its upper surface and a pair of mating receivers 104a, 104b formed at its opposite ends. The mounting feet 401 (FIG. 7) of the interface members rest on the top of the litter poles, thus, a catch assembly 131, shown in FIG. 8, is affixed to horizontal frame member 106 using mounting rail 102b and block 132 which has receiver 104c formed longitudinally within it. Affixed to or formed on block 132 is a clevis 133 which receives a pivot pin 134 which passes through a catch lever 136 such that the lever 136 is captured within the clevis yet free to rotate about the pin 134. Lever 136 carries a pair of opposing lock collars 137 to which a double armed J strap 138 is pivotally mounted such that it can hang from collars 137 and partially engage a litter pole. With the J strap 138 positioned beneath the litter pole, the lever 136 can be pivoted upwardly to an over-center position to bring the J-strap 138 into gripping engagement with the litter pole, thus capturing the litter pole between the J-strap 138 on the bottom and the mounting feet on the top of the litter pole as seen in FIGS. 7 and 8. Spring loaded locking collar 140 includes a rear lip 141 that prevents rotation of lever 136 until the internal spring (not shown) is compressed. Lever 136 may have a compression spring captured within slot 139 such that the J-strap properly seats against the litter pole and may have a storage slot 130 transversely formed in cap 142 storing the J strap 138.

Figure 10:
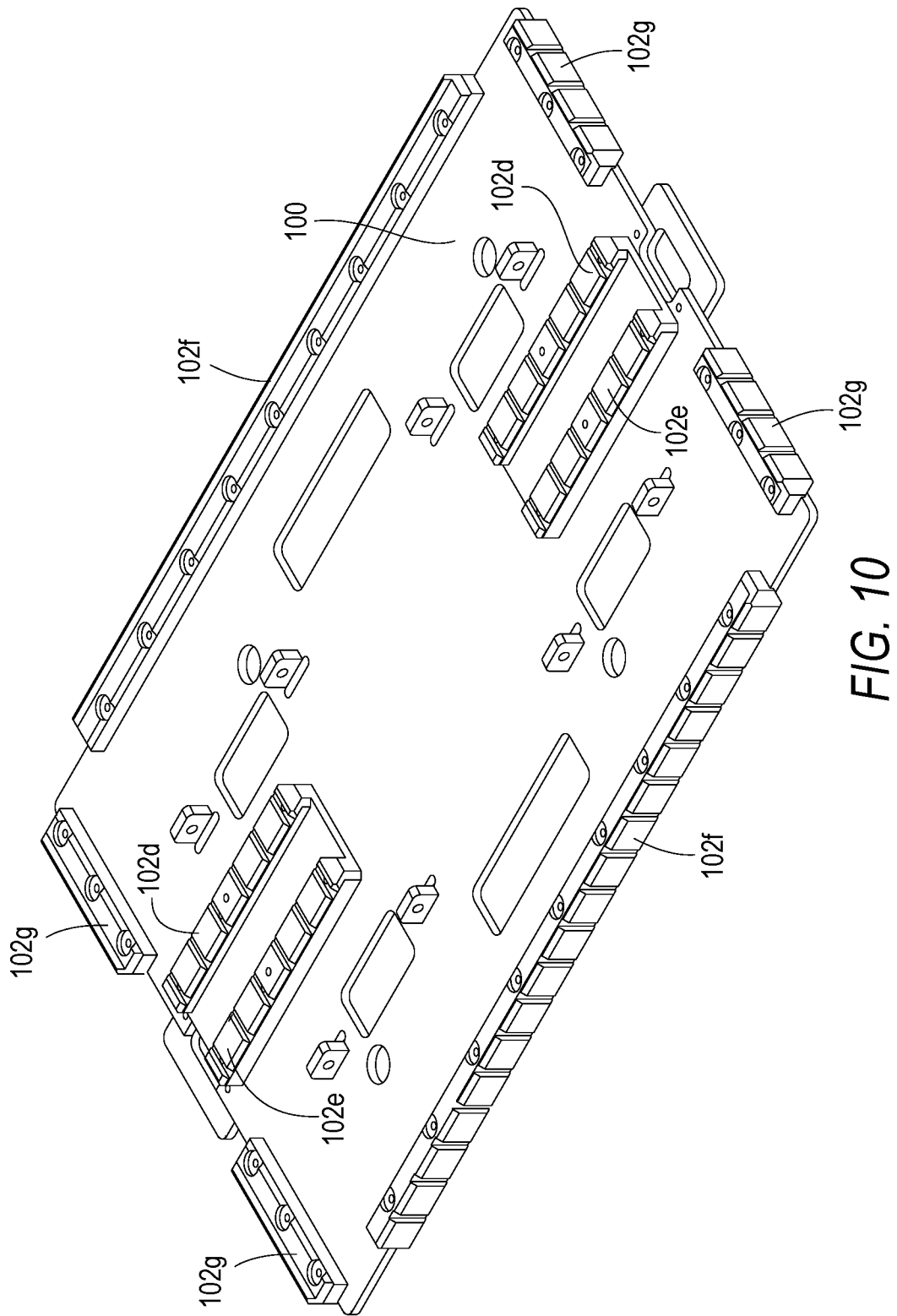
FIG. 10 is a perspective view of an equipment mounting plate.
Figure 16:
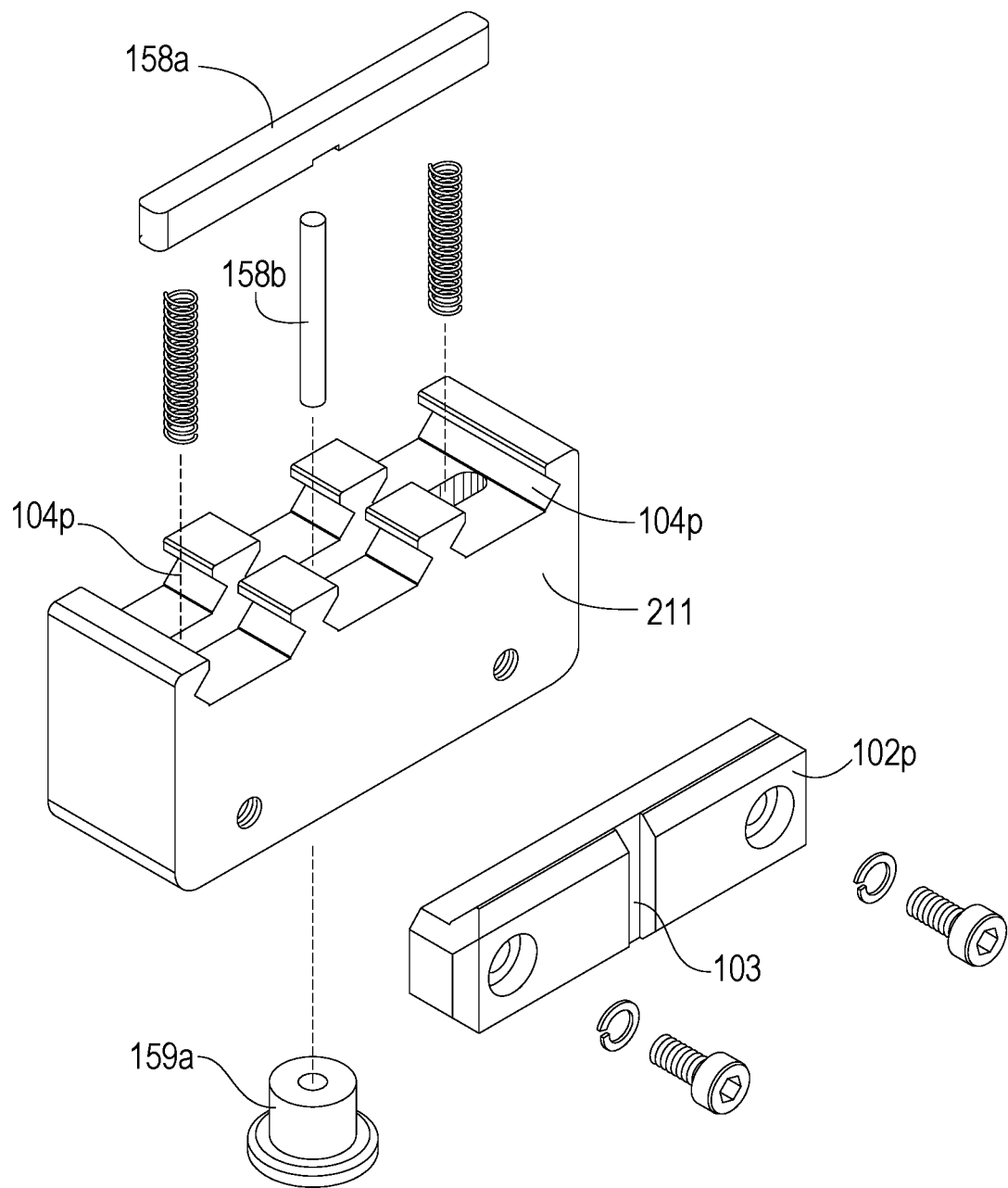
FIG. 16 is view of a directional changer.
Figure 17:
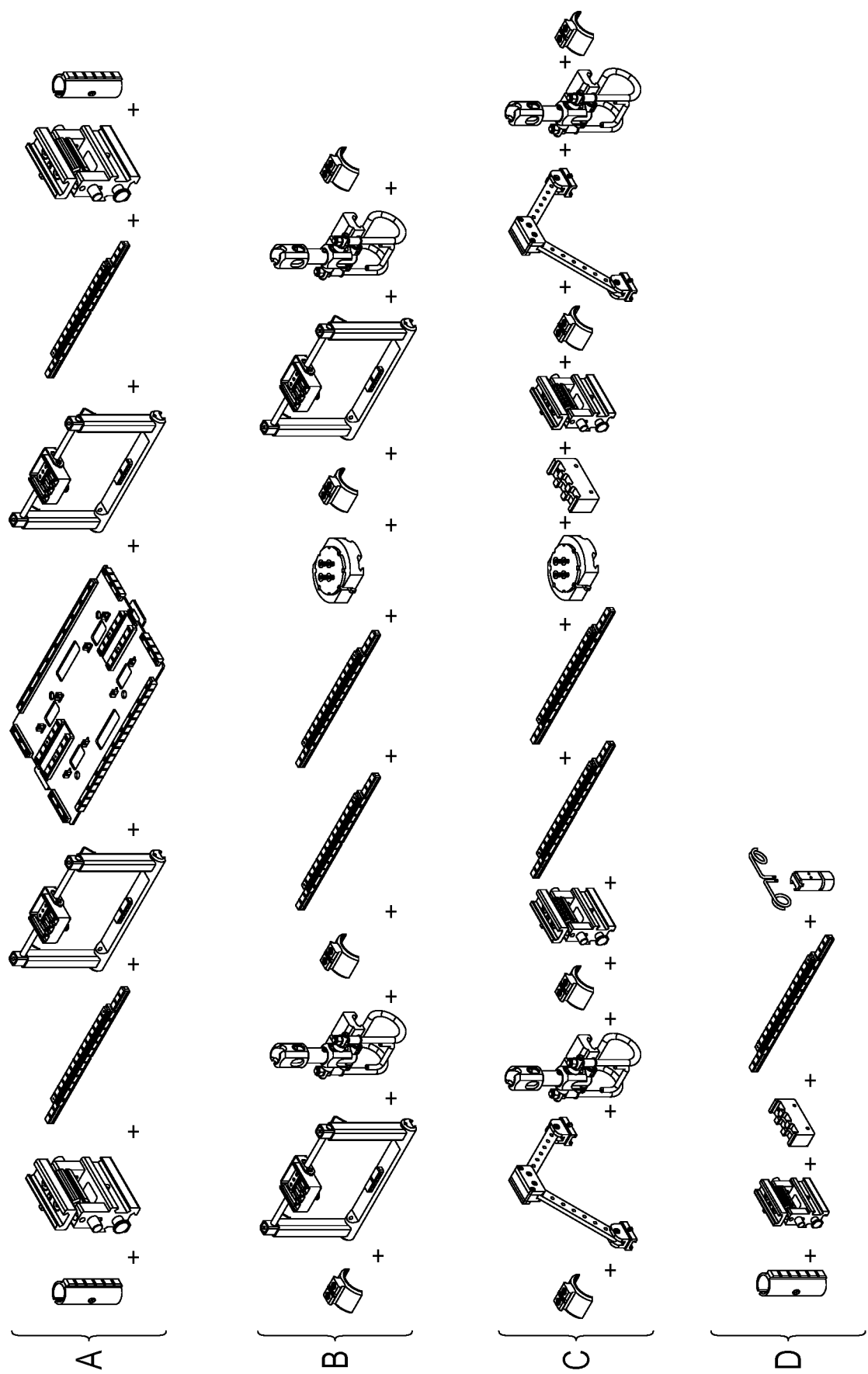
FIGS. 17A to 17D show multiple combinations possible with the modular system, wherein the combinations of modular units are indicated by a plus sign.

At the upper ends of legs 113 and 114 a rod 161 is mounted parallel to and spaced from horizontal frame member 106 as seen most clearly in FIGS. 5 and 6. Rod 161 passes through two legs 165 of latch block 162 and the body 163 of barrel lock. Each latch block 162 has a plurality of spaced apart receivers 104d & 104e formed therein which mate with mounting rails 102d & 102e that are affixed to the underside of a platform as shown in FIG. 10. The locking mechanism for these receivers, illustrated more clearly in FIG. 16, is a spring biased transverse locking bar 158a connected to a rod 158b and urged into the cavity of the receivers. A knob 159a is connected to the rod 158b to enable one to pull on the knob, compress the spring and withdraw the locking bar to insert the rails.

Also supported by the legs 165 of latch block 162 is a spring biased latch bar 164 which extends through slots in the legs 165 of latch body 162. A pair of springs captured in spring wells 160 in the legs 165 urge the latch bar 164 toward the lock barrel body 163. Lock barrel body 163 has a pair of grooves 166 offset by 90 degrees into which latch bar 164 is selectively biased to lock the latch block into position. Release handle 167 includes arms 168 which engage the ends of latch bar 164. Slots 169 formed in the arms 168 as shown in FIGS. 5 and 6 such that rod 161 passes there through yet handle 167 is free to move transversely of rod 161 to push latch pin 164 into a release position such that latch block 162 is free to rotate about rod 161 relative to lock barrel body 163. The grooves 166 is bordered by beveled surfaces, such that when release handle is rotated the latch pin moves in the slots to release the latch body and allow the supports 110 and 111 to pivot selectively approximately 90 degrees relative to the latch block and thence 90 degrees relative to a platform secured to latch block 162 between a supporting position and a stowed position.

Referring to FIG. 10, the platform also has a number of mounting rails 102*f* and 102*g* affixed to the sides or edges thereof to which the aforementioned medical devices may be attached for support. The platform may also have a number of mounting holes formed therein as shown in FIG. 5 of U.S. Pat. No. 6,493,890 which is incorporated herein by reference. It should be understood that when rapid jump unit assemblies are deployed on each litter pole, the platform can be supported across the litter at a selected height by engagement with the latch block 162 of each rapid jump unit assembly, however, this is only one embodiment of the invention.

Figure 9:
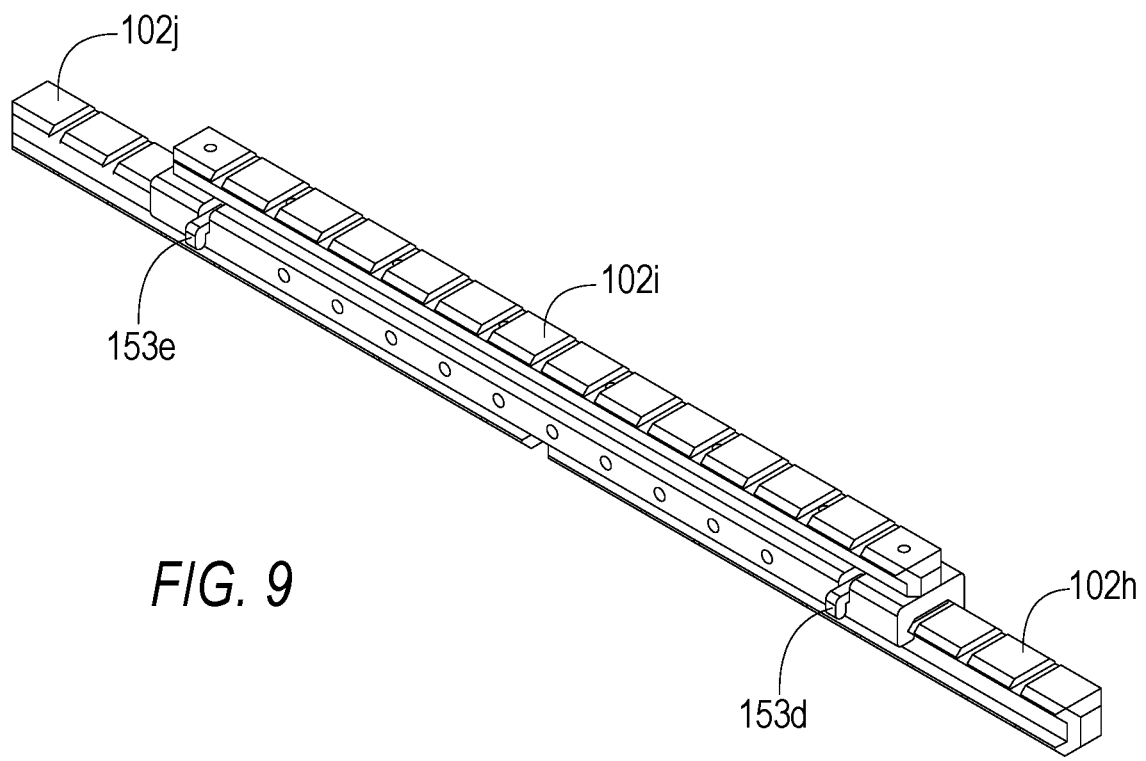
FIG. 9 is a perspective view of my expansion rail assembly.
Figure 11:
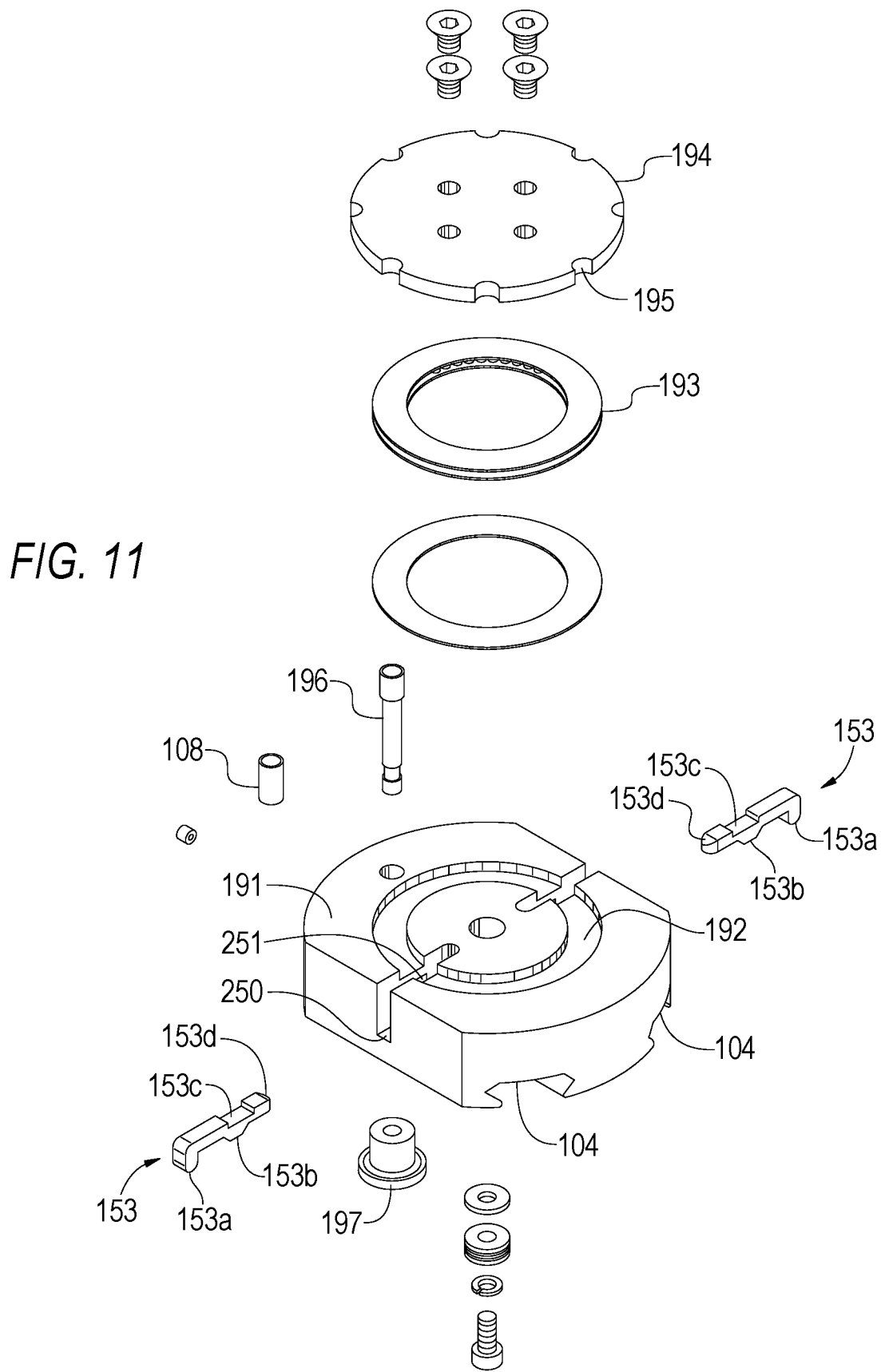
FIG. 11 is an exploded perspective view of a cradle mounting assembly.
Figure 11A:
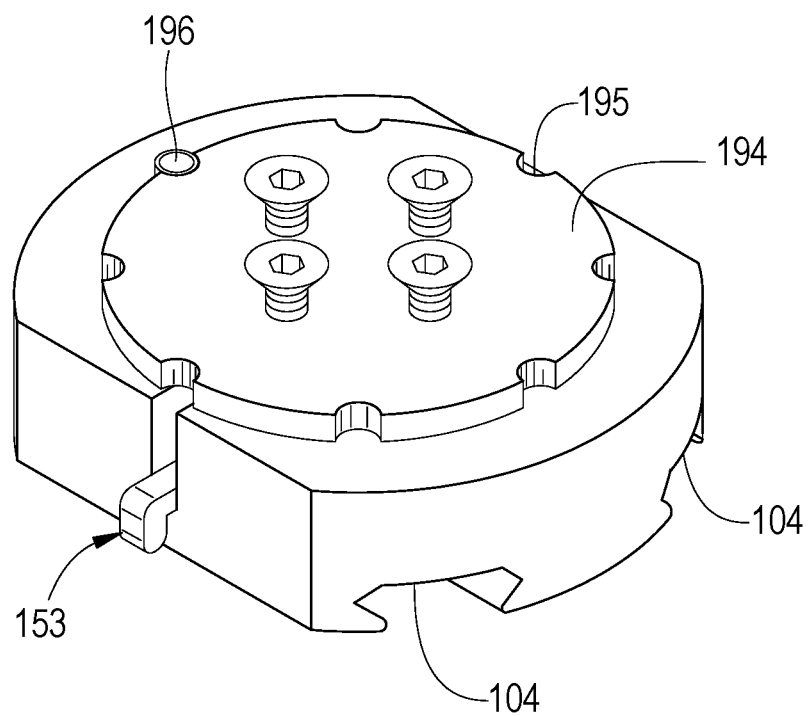
FIG. 11A is an assembled view of the cradle mounting assembly of FIG. 11.

Referring to FIG. 9, it will be seen that expansion rails 102*h*, 102*i* and 102*j* may be provided in sets. The expansion rails may be connected to each other using lock pins 153*d* and *e* as previously explained. As many sets of expansion rails may be used as may be needed, thus, the expansion rails may be engaged with latch blocks from rapid jump unit assemblies on each side of the litter to provide a different mounting structure for medical equipment. By way of example a medical monitoring device may need to be placed on the structure and repositioned so that an attending care giver can see the monitor display. In such a situation, a cradle as shown in FIGS. 11 and 11*a* can be used on rails 102. Cradle base 191 has formed within it a pair of receivers 104 into which rails 102 may be locked by locking pins 153 as previously discussed. The base 191 includes a race 192 for a set of bearings 193 and a mounting plate 194 which are all conventionally connected. Mounting plate 194 has a series of spaced apart recesses about its circumference that are engaged by spring biased pin 196 as a locking mechanism to secure the mounting plate in position. It will be understood that a monitor or other device would sit atop a tray connected to the cradle mounting plates by fasters such as the four bolts shown in the figures. While the present cradle may be used for monitors and with any manner of connection required such as straps and clamps, it is also to be understood that the disclosed rail and receiver concept is readily adapted to provide connection to other medical equipment, device(s), and/or container(s) such as pumps, ventilators, suction units, IV bags, oxygen bottles to be attached to the litter separately from the platform.

Figure 14:
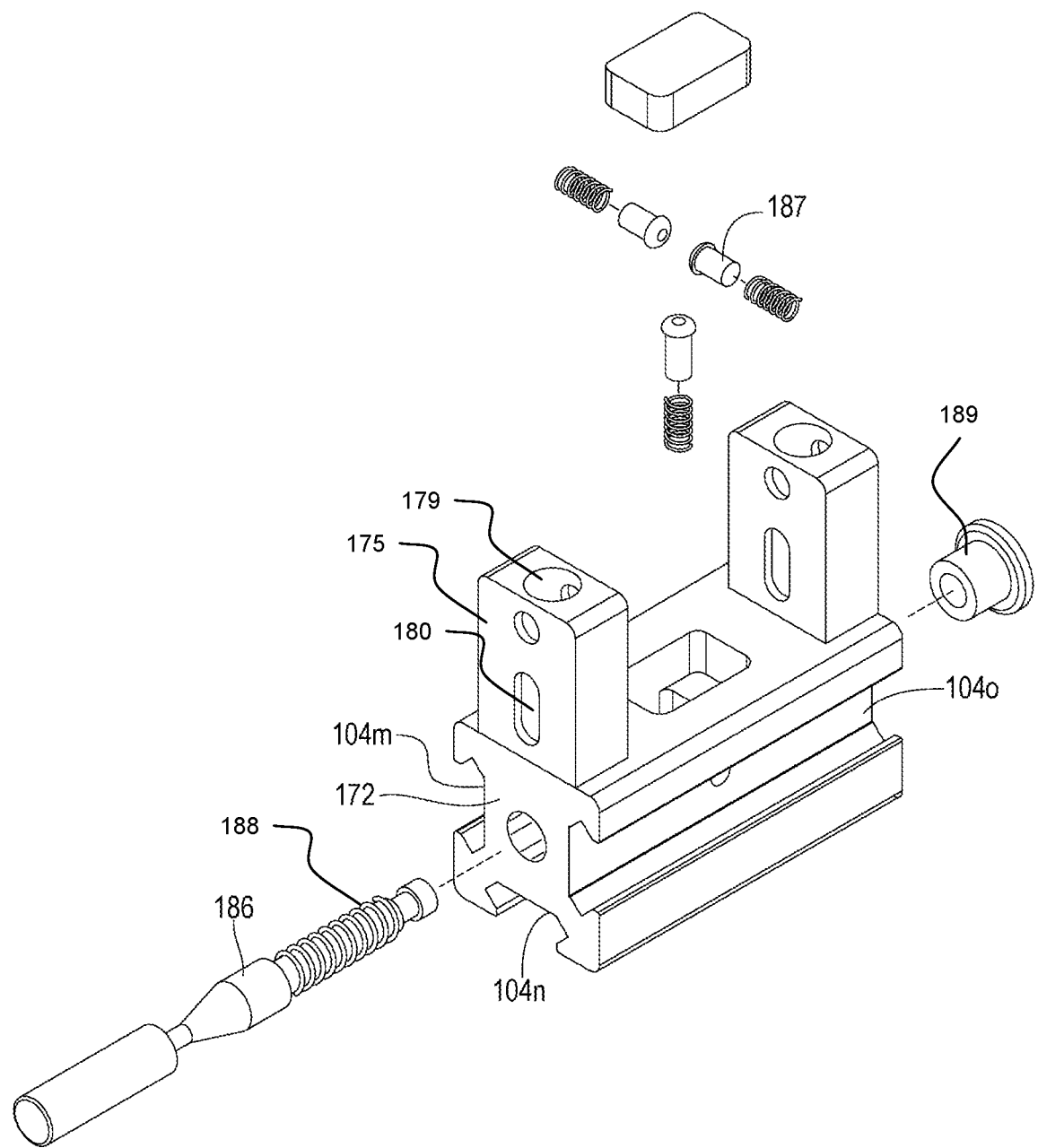
FIG. 14 is an exploded perspective view of a triple rail adapter.
Figure 15:
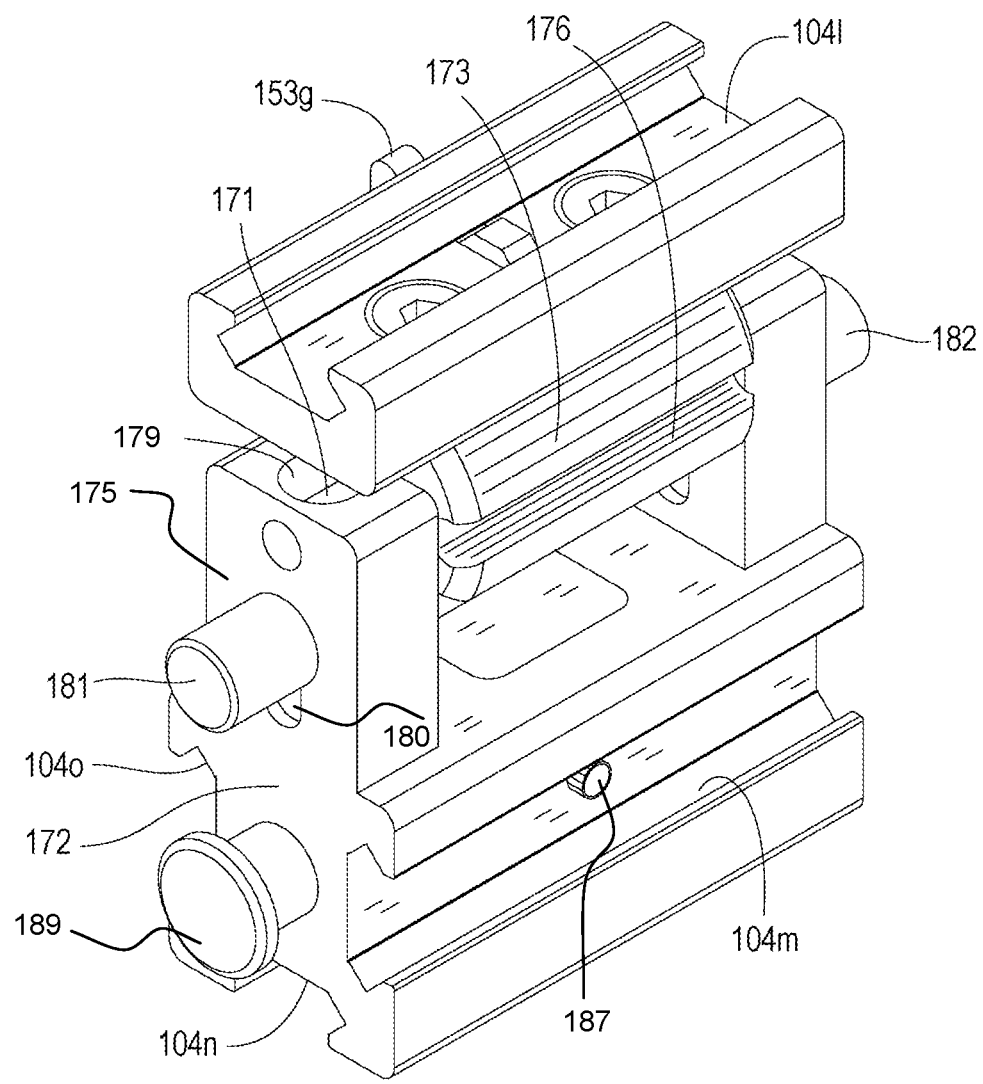
FIG. 15 is a perspective view of a triple rail adapter.

Likewise, multiple sets of expansion rails 102*h*, 102*i* and 102*j* may be used in combination to extend along either side of the litter between pair of litter interfaces such as sleeves 101 or clamps 201. To facilitate such structures I provide additional connectors, such as a triple rail connector and a single rail connector shown in FIGS. 14-15. The single rail connector and the triple rail connector shown in FIG. 15 are in many ways similar in operation to the latch mechanism of the rapid jump assembly. Rail connector rod 171 passes through two legs 175 of rail block 172 and the body 173 of rail connector barrel lock. The rail block 172 has three receivers 104*m*, 104*n* and 104*o*, aligned parallel to each other and oriented 90 degrees from each other. Each receiver can engage with a separate mounting rail 102. Rails positioned in the receivers can be engaged by another embodiment of the locking member as shown in FIGS. 14 and 15. Captured concentrically of the three receivers within rail block 172 is a lock rod 186 which has a portion thereof tapered to a narrower diameter. Also captured within rail block 172 are three inwardly biased pins 187 which extend through apertures into receivers 104*m*, *n*, and *o*. Lock rod 186 is biased by a concentric spring 188 such that the major diameter of the lock rod forces the pins outwardly into the receivers. Lock rod 186 is axially movable by pulling on knob 189 or pushing on the opposite end of lock rod 186 to align the tapered portion with the pins, thus allowing them to retract from the receivers 104 and disengage from any slot 103 within the receivers simultaneously. In the single rail version a lock mechanism using a locking pin 153 is used.

Also supported by the legs 175 of rail block 172 is a spring mounted latch rod 174 which extends through slots in the legs 175 of rail block 172. Rail barrel lock body 173 has a plurality of grooves 176 offset by 45 degrees into which a latch rod is selectively biased by a spring mounted in spring well 179 to lock the rail block into position. A pair of actuator knobs 181 and 182 engage the ends of the latch rod. Slots 180 formed in the legs 175 such that the latch rod to connects to knobs 181 and 182 and is movable within the slot to disengage from rail barrel lock body 173 and allow the rail block to be reoriented relative thereto. Rail barrel lock body has a rail receiver 104*l* secured to it with a locking mechanism using lock pin 153*g*, therefore a rail 102 secured in any of the three receivers 104*m*, *n* or *o*, can be incrementally offset from a rail in receiver 104*l*. Thus, if an extension rail set is connected to a litter interface members 101 or 201 by using a single rail or triple rail connector, a railing may be formed alongside the litter which can be tilted outwards away from the litter as medically needed.

At times it may be necessary to change the direction of the rails thus I also provide a directional changer as shown in FIG. 16 which is simply a changer body 211 with three parallel receivers 104*p* formed on one face and a rail 102*p* formed on an orthogonal face extending perpendicular to the receivers 104*p*. The locking mechanism associated with the receivers is the same as is used in the latch block 162, namely a spring biased transverse locking bar 158*a* connected to a rod 158*b* and urged into the cavity of the receivers 104*p*. A knob 159*a* is connected to rod 158*b* to enable one to pull on the knob 159*a*, compress the springs and withdraw the locking bar 158*a* from the receivers 104 to insert one or more rails 102. The lock bar 158*a* seats in groove 103 to hold the inserted rails 102 in place.

Figure 12:
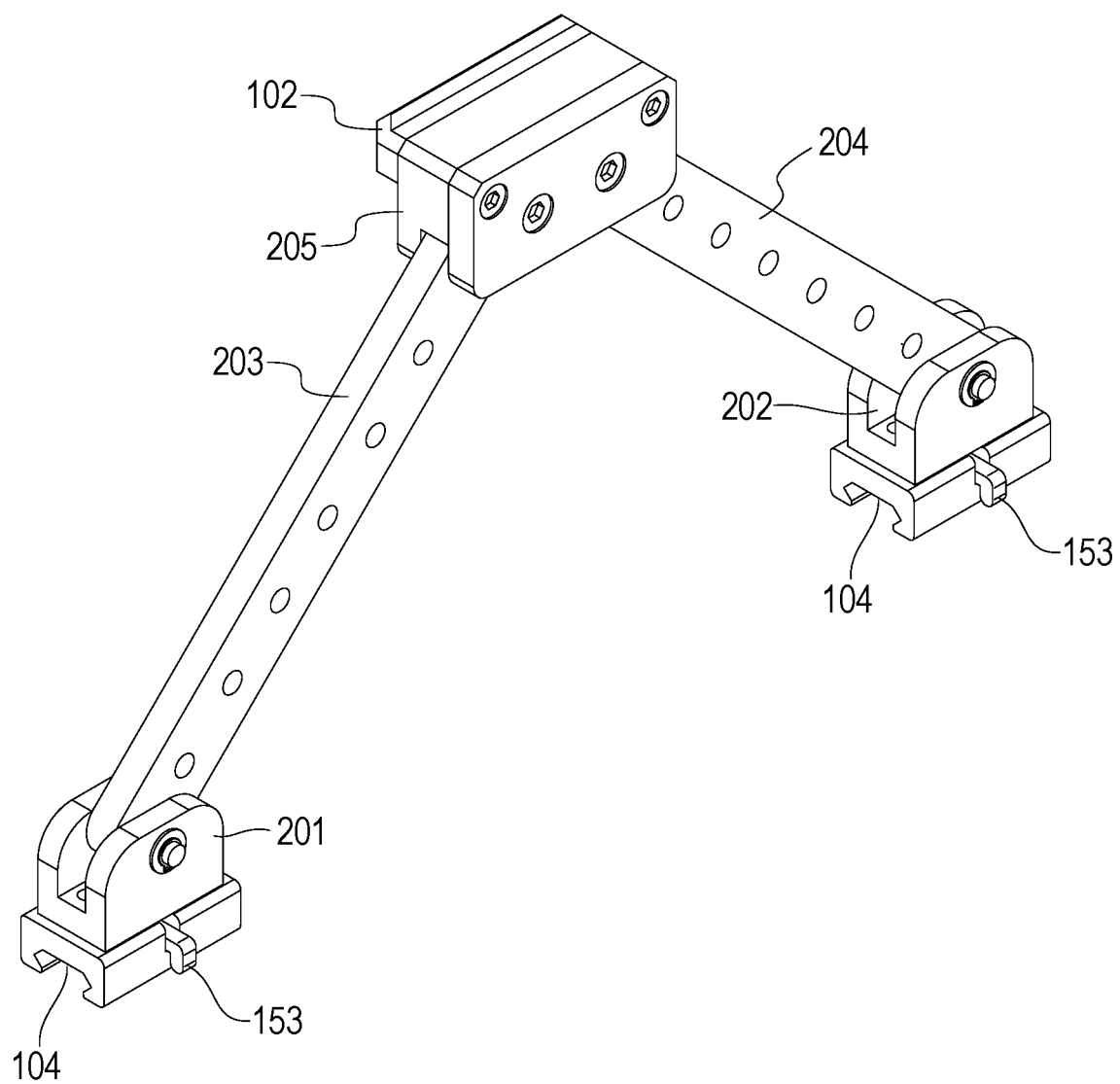
FIG. 12 is a perspective view of an A frame assembly.

In some instances it may be desirable to use a more robust structure, therefore I provide an A frame vertical assembly, as shown in FIG. 12, that can be used instead of the rapid jump unit assembly. The A frame vertical assembly is also based on a pair of receivers 104 which engage a rail 102 and lock thereto with locking pin 153. The rail 102 may be part of a side assembly as described above or may be a rail 102 supported between two interfacing feet 401 and clamped to the litter by a catch assembly 131. The receivers support clevis's 201 and 202 to which the lower ends of a pair of legs 203 and 204 are pivotally mounted. The upper ends of legs 203 and 204 are pivotally connected to a base box 205 which constrains the legs 203 and 204 to separate at no greater than a 90 degree angle. Affixed to the base box 205 is a standard rail 102*q*. It will be noted in the drawings that the rail 102 is oriented horizontally on the side of the base box 205. A build out using the A frame could use a single or three way rail connector mounted to rail 102*q* with a directional changer mounted in receiver 104. By rotating the rail connector 90 degrees and locking it in position, the three rail receivers of the directional changer are oriented to receive one or more rails 102 extending across the litter, thereby providing mounting space above the litter. Accessories such as the cradle base 191 or any other device can be mounted on a build out from the A frame vertical assembly.

Figure 13:
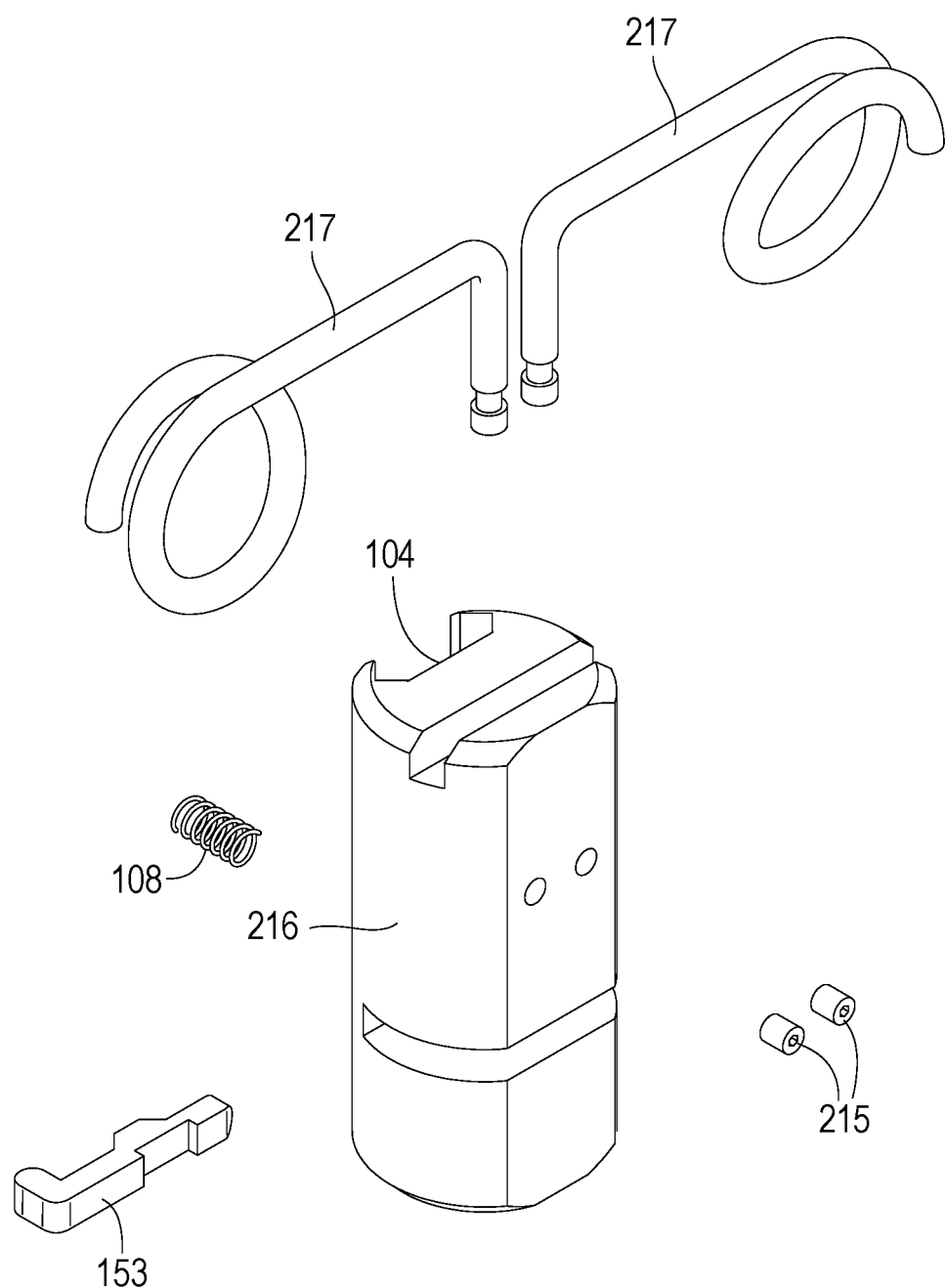
FIG. 13 is an exploded perspective view of an IV support.

It should be noted that a build out may simply have a vertical component. By way of example, a need will almost always exist for an IV hanger at a height above the litter. It should be understood that litter adapters 101 and 201 can easily support such a hanger simply by affixing rail adapter and a directional changer to either of them and inserting a rail extension assembly therein. An IV hanger 215 such as shown in FIG. 13. As seen in FIG. 13 IV hanger 215 includes a tubular base 216 into which a pair of formed stainless steel IV hooks 217 are inserted. The hooks may be held in place by set screws or any other conventional manner. Tubular base 216 includes a receiver 104*r* into which a rail 102 can be inserted and locked into position by lock pin 153*r*.

In the preceding paragraphs, I have discussed securing a platform to a litter, securing side mounting rails to a litter, securing bridge mounting rails across a litter, securing monitoring equipment mounted on a rotatable cradle to either a bridge built with a rapid jump unit assembly or an A frame assembly, and vertical mounting of accessories such as an IV holder. The combination of disclosed elements is displayed in FIGS. 17A to 17D wherein 17A depicts one combination of elements, 17B another, 17C yet another, and 17D a fourth combination. However, these are not all of the possible combinations available with my modular system. It should be clear that through the use of standardized rails and receivers and locking elements to connect the receivers as well as rail adapters and direction adapters to change the orientation of the rails, a care giver can build on the litter almost any configuration structure necessary, without sacrificing access to the patient as was necessary in the devices shown in my earlier patents.

While in the foregoing specification this invention has been described in relation to certain embodiments thereof, and many details have been put forth for the purpose of illustration, it will be apparent to those skilled in the art that the invention is susceptible to additional embodiments and that certain of the details described herein can be varied considerably without departing from the basic principles of the invention.

What I claim is:

1. An apparatus for mounting medical equipment to litters, comprising:
    a plurality of litter interface members configured to engage a component of a litter to releasably secure the apparatus to the litter;
    a plurality of rails having a plurality of securing slots formed therein at measured distances along said plurality of rails, wherein at least one of said plurality of rails is affixed to an exterior of each of said plurality of interface members; and
    at least one lock mechanism, the at least one lock mechanism comprising a channel therein and at least one movable member, the channel accepting a selected one of the plurality of rails, and the at least one movable member biased to selectively engage a selected one of the plurality of securing slots of the selected one of the plurality of rails to lock the selected one of the plurality of rails within the at least one channel.

2. An apparatus as defined in claim 1, further comprising a plurality of connecting members defining a set of rail receiving channels therein to connect one or more of said rails together to form a frame when supported on a litter and upon which medical equipment can be attached.

3. An apparatus as defined in claim 2, wherein some of said plurality of connecting members have some of said set of receiving channels formed therein transverse to others of said set of receiving channels.

4. An apparatus as defined in claim 2, wherein one or more of said plurality of connecting members have at least two parallel receiving channels formed therein with one of said at least two parallel receiving channels pivotally connected for selective movement about an axis parallel to each of said at least two parallel channels.

5. An apparatus as defined in claim 1, further comprising:
    a first vertical assembly mounted to two of said plurality of litter interface members and secured thereto by one or more of said at least one lock mechanism;
    a second vertical assembly mounted to two other of said plurality of litter interface members and secured thereto by one or more of said at least one lock mechanism; and
    a horizontal equipment mounting member secured between said first and second vertical assemblies.

6. An apparatus as defined in claim 5, wherein said first and second vertical assemblies comprise rapid jump unit assemblies.

7. An apparatus as defined in claim 5, wherein said horizontal equipment mounting member comprises a platform having a plurality of rails secured to the edges thereof.

8. An apparatus as defined in claim 5, wherein said horizontal equipment mounting member comprises at least one rail extension member.

9. An apparatus as defined in claim 5, wherein said first and second vertical assemblies comprise A frame assemblies.

10. An apparatus as defined in claim 9, wherein said horizontal equipment mounting member comprises at least one rail extension member.

11. An apparatus as defined in claim 9, wherein said horizontal equipment mounting member comprises a platform having a plurality of rails secured to edges thereof.

12. An apparatus as defined in claim 5, further comprising a cradle for a medical device mounted to said horizontal equipment mounting member.

13. An apparatus as defined in claim 1, further comprising:
    a connecting member defining a first rail receiving channel therein and having one of said plurality of said rails affixed to one of said plurality of litter interface members received in said first rail receiving channel and secured therein by a first of said at least one locking mechanism;
    a second connecting member defining a second rail receiving channel therein and having one of said plurality of said rails affixed to another of said plurality of litter interface members coaxially aligned with said one of said plurality of interface members received in said second rail receiving channel and secured therein by a second of said at least one locking mechanism; and
    at least one rail extension assembly received within selected channels of said first and second connecting members and secured to respective first or second connecting members by separate at least one locking mechanisms such that said at least one rail extension is mounted in position to mount medical equipment thereon.

14. An apparatus as defined in claim 1, further comprising a litter, wherein at least one of said plurality of litter interface members engages with a component of said litter to secure the apparatus to said litter.

15. A modular system for mounting equipment to underlying surfaces, comprising:
  at least one interface member configured to engage an underlying surface to secure the modular system thereto,
  a plurality of rails having one or more slots formed transversely therein, each of said rails being attached to an exterior of a respective one of said at least one interface member; and
  a plurality of receivers for said rails, each receiver of said receivers comprising a receiving channel that receives a respective one of said rails and a locking member associated therewith to selectively engage said one or more slots of said respective one of said rails to secure said receiver to said respective one of said rails.

16. A modular system according to claim 15, wherein each locking member comprises at least one movable member biased in a corresponding receiving channel to selectively engage a selected one of the one or more slots to lock a selected one of the plurality of receivers to a selected one of the plurality of rails.

17. A modular system according to claim 15, further comprising the underlying surface, wherein said at least one interface member engages the underlying surface to secure the modular system to the underlying surface.

18. A modular system according to claim 17, wherein the underlying surface is a litter.

19. A modular system according to claim 18, further comprising a plurality of connecting members that each comprise a respective one of said receivers therein to connect one or more of said rails together to form a frame supported on said litter upon which said medical equipment can be attached.

20. A modular system according to claim 17, wherein said at least one interface member releasably secures the modular system to the underlying surface.

21. A modular system according to claim 15, wherein one of said receivers comprises a first vertical assembly, and wherein another one of said receivers comprises a second vertical assembly,
  the system further comprising a horizontal equipment mounting member secured between said first and second vertical assemblies.

22. A modular system according to claim 15, wherein each of said plurality of rails and plurality of receivers are integrated into a structural component comprising one of connectors, directional changers, rail extenders, platforms, bases, interfaces, or vertical assemblies, whereby said structural components are selectively interconnected on said underlying surface in close proximity to a patient on said underlying surface to provide selectively configurable mounting for said medical equipment relative to said underlying surface.

* * * * *